(12) United States Patent
Rezach et al.

(10) Patent No.: US 11,026,723 B2
(45) Date of Patent: Jun. 8, 2021

(54) PEDICLE SCREW ASSEMBLIES WITH 3D PRINTED COMPONENTS

(71) Applicant: WARSAW ORTHOPEDIC, INC., Warsaw, IN (US)

(72) Inventors: William Alan Rezach, Covington, TN (US); Jason M. May, St. Johns, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 16/380,739

(22) Filed: Apr. 10, 2019

(65) Prior Publication Data
US 2020/0323563 A1 Oct. 15, 2020

(51) Int. Cl.
| A61B 17/70 | (2006.01) |
| B33Y 80/00 | (2015.01) |
| A61B 17/00 | (2006.01) |

(52) U.S. Cl.
CPC .......... *A61B 17/7034* (2013.01); *B33Y 80/00* (2014.12); *A61B 2017/00526* (2013.01)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS

| 7,947,065 B2 | 5/2011 | Hammill, Sr. et al. |
| 8,075,603 B2 | 12/2011 | Hammill, Sr. et al. |
| 8,465,530 B2 | 6/2013 | Hammill, Sr. et al. |
| 8,663,291 B2 | 3/2014 | Doubler et al. |
| 9,060,814 B2 | 6/2015 | Doubler et al. |
| 9,615,858 B2 | 4/2017 | Doubler et al. |
| 9,707,013 B2 | 7/2017 | Rezach et al. |
| 9,872,711 B2 | 1/2018 | Hynes et al. |
| 9,883,948 B2 | 2/2018 | Chavarria et al. |
| 9,949,776 B2 | 4/2018 | Mobasser et al. |
| 9,962,171 B2 | 5/2018 | Rezach et al. |
| 9,974,569 B2 | 5/2018 | Lehmann, Jr. et al. |
| 9,993,270 B2 | 6/2018 | Butler |
| 10,028,770 B2 | 7/2018 | Rezach et al. |

(Continued)

FOREIGN PATENT DOCUMENTS

| CN | 104523342 | 4/2015 |
| JP | 2004-512899 | 4/2004 |

OTHER PUBLICATIONS

U.S. Appl. No. 15/843,938, filed Dec. 15, 2017 in the name of May et al.

(Continued)

*Primary Examiner* — Julianna N Harvey

(57) ABSTRACT

A bone fastener assembly including a bone screw, a receiver, a crown, a first retaining ring, and a second retaining ring is provided. The crown is received in an interior cavity of the receiver, and the first retaining ring is provided to hold the crown in the receiver. At least a portion of a head portion is received in the interior cavity of the receiver, and the second retaining ring is provided to hold at least a portion of the head portion in the receiver. The crown, the first retaining ring, and/or the second retaining ring can be manufactured using a 3D printing process that provides a higher surface finish (Ra).

20 Claims, 4 Drawing Sheets

FIG. 4

(56) References Cited

U.S. PATENT DOCUMENTS

| | | | |
|---|---|---|---|
| 10,172,650 | B2 | 1/2019 | Hynes et al. |
| 10,258,385 | B1 | 4/2019 | Doubler et al. |
| 10,285,738 | B1 | 5/2019 | Doubler et al. |
| 2002/0026193 | A1* | 2/2002 | Barker ............... A61B 17/7037 606/328 |
| 2006/0241596 | A1 | 10/2006 | Rezach |
| 2007/0233138 | A1 | 10/2007 | Figueroa et al. |
| 2011/0313466 | A1* | 12/2011 | Butler ............... A61B 17/7064 606/279 |
| 2012/0065691 | A1 | 3/2012 | Simonson |
| 2012/0270180 | A1 | 10/2012 | Dahlstrom et al. |
| 2017/0197014 | A1 | 7/2017 | McEntire et al. |
| 2017/0245898 | A1 | 8/2017 | May et al. |
| 2017/0333085 | A1* | 11/2017 | Jackson ............... A61B 17/863 |
| 2018/0206890 | A1 | 7/2018 | Rezach |

OTHER PUBLICATIONS

U.S. Appl. No. 16/287,700, filed Feb. 27, 2019 in the name of Rezach et al.
U.S. Appl. No. 16/386,328, filed Apr. 17, 2019 in the name of Rezach et al.
U.S. Appl. No. 16/395,319, filed Apr. 26, 2019 in the name of Wickham et al.
U.S. Appl. No. 16/395,409, filed Apr. 26, 2019 in the name of Wickham et al.
International Search Report and Written Opinion dated Feb. 11, 2020 from corresponding International Application No. PCT/US2019/057576.
International Search Report dated Feb. 6, 2020 from corresponding International Application No. PCT/US2019/057184.
Written Opinion dated Feb. 6, 2020 from corresponding International Application No. PCT/US2019/057184.

* cited by examiner

PEDICLE SCREW ASSEMBLIES WITH 3D PRINTED COMPONENTS

FIELD

The present technology is generally related to a pedicle screw assembly having 3D printed components.

BACKGROUND

Pedicle screw assemblies are used to facilitate placement and attachment of spinal rods relative to the spine. The spinal rods can be used in correcting spinal abnormalities. Typically, such pedicle screw assemblies include at least a bone screw portion and a receiver portion attached to one another. The bone screw portions are attached to vertebrae, and the receiver portions receive portions of the spinal rods. Furthermore, the receiver portions of typical pedicle screw assemblies are angularly and fixedly positionable with respect to the screw portions to afford attachment of the spinal rods between vertebrae. The configurations of pedicle screw assemblies oftentimes include competing trade-offs. For example, decapitation strength of receiver portions relative to the bone screw portions, and maximum angulation of the receiver portions relative to the bone screw portions are competing trade-offs. Typically, as the maximum angulation of the receiver portions relative to the bone screw portions is increased, the decapitation strength is decreased. Therefore, there is a need for a manufacturing technique that can mitigate this and increase other performance characteristics of the pedicle screw assemblies.

SUMMARY

The techniques of this disclosure generally relate to one or more 3D printed components usable in fastener assemblies including pedicle screw assemblies.

In one aspect, the present disclosure provides a bone fastener assembly including a bone screw including a head portion, a threaded shaft portion, and a central axis, the head portion including an exterior surface; a receiver including a body portion, a first arm portion, and a second arm portion, the body portion having a first end, an opposite second end, and an interior surface defining a first cavity extending between the first end and the second end, the first arm portion including a first interior arm surface and the second arm portion including a second interior arm surface, the first interior arm surface and the second interior arm surface defining a second cavity therebetween, the first cavity and the second cavity communicating with one another; a crown including a first end, an opposite second end, an exterior surface, and an interior surface defining at least a first interior cavity portion extending from the first end of the crown to a position intermediate the first end and the second end of the crown; and a retaining ring having an annular shape and including a generally cylindrical exterior surface and an upwardly-facing surface; where, when the bone fastener assembly is assembled, at least a portion of the crown is positioned within the first cavity of the receiver at a position at and adjacent the second end of the body portion, the retaining ring is positioned within the first cavity of the receiver at a position between the crown and the first end of the body portion, at least a portion of the head portion is receivable between the crown and the retaining ring, and the exterior surface the head portion contacts the upwardly-facing surface of the retaining ring, and where the retaining ring is manufactured using a 3D printing process that provides for a Ra (Surface Finish) of at least the upwardly-facing surface of the retaining ring ranging from about 0.8 μm (32 μin) to about 3.2 μm (125 μin).

In another aspect, the disclosure provides a bone fastener assembly including a bone screw including a head portion, a threaded shaft portion, and a central axis, the head portion including an exterior surface; a receiver including a body portion, a first arm portion, and a second arm portion, the body portion having a first end, an opposite second end, and an interior surface defining a first cavity extending between the first end and the second end, the first arm portion including a first interior arm surface and the second arm portion including a second interior arm surface, the first interior arm surface and the second interior arm surface defining a second cavity therebetween, the first cavity and the second cavity communicating with one another; a crown including a first end, an opposite second end, an exterior surface, and an interior surface defining at least a first interior cavity portion extending from the first end of the crown to a position intermediate the first end and the second end of the crown; a retaining ring having an annular shape and including a generally cylindrical exterior surface and an upwardly-facing surface; and an expansion ring having an annular shape and a including a generally cylindrical exterior surface and a generally cylindrical interior surface; where, when the bone fastener assembly is assembled, the retaining ring is positioned within the first cavity of the receiver at a position between the crown and the first end of the body portion, the expansion ring is positioned within the first cavity of the receiver at a position between the second end of the body portion and the retaining ring; at least a portion of the crown is received within the expansion ring; at least a portion of the head portion is receivable between the crown and the retaining ring, and the exterior surface the head portion contacts the upwardly-facing surface of the retaining ring, and where the retaining ring is manufactured using a 3D printing process that provides for a Ra (surface finish) of at least the upwardly-facing surface of the retaining ring ranging from about 0.8 μm (32 μin) to about 3.2 μm (125 μin).

In yet another aspect, the disclosure provides a bone fastener assembly including a bone screw including a head portion, a threaded shaft portion, and a central axis, the head portion including an exterior surface; a receiver including a body portion, a first arm portion, and a second arm portion, the body portion having a first end, an opposite second end, and an interior surface defining a first cavity extending between the first end and the second end, the first arm portion including a first interior arm surface and the second arm portion including a second interior arm surface, the first interior arm surface and the second interior arm surface defining a second cavity therebetween, the first cavity and the second cavity communicating with one another; and a retaining ring having an annular shape and including a generally cylindrical exterior surface and an upwardly-facing surface; where, when the bone fastener assembly is assembled, the retaining ring is positioned within the first cavity of the receiver at a position between the first end and the second end of the body portion, at least a portion of the head portion is receivable between the retaining ring and the second end of the body portion, and the exterior surface the head portion contacts the upwardly-facing surface of the retaining ring, and where the retaining ring is manufactured using a 3D printing process that provides for a Ra (surface finish) of at least the upwardly-facing surface of the retaining ring ranging from about 0.8 μm (32 μin) to about 3.2 μm (125 μin).

The details of one or more aspects of the disclosure as set forth in the accompanying drawings and the description below. Other features, objects, and advantages of the techniques described in this disclosure will be apparent from the description and drawings, and from the claims.

DETAILED DESCRIPTION

Figure 1:
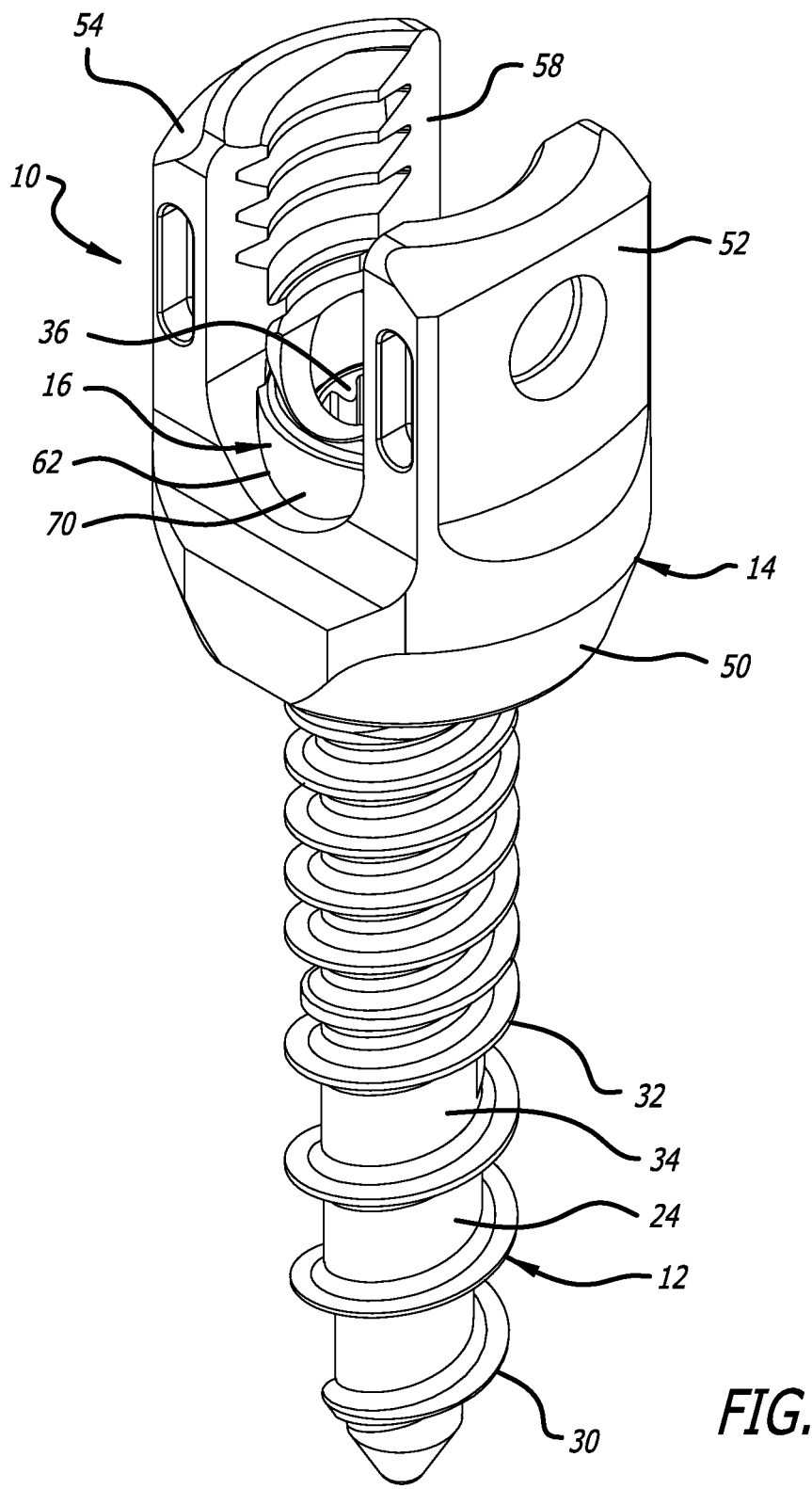
FIG. 1 is a top, front perspective view that illustrates an embodiment of a pedicle screw assembly.

A fastener assembly according to an embodiment of the present disclosure is generally indicated by the numeral 10 in FIGS. 1-4. The fastener assembly 10 includes a screw 12, a receiver 14, a crown 16, a first expansion (or retaining) ring 18, and a second expansion (or retaining) ring 19. As discussed below, the fastener assembly 10 is used in facilitating attachment of a spinal construct such as a spinal rod S to the spine. As discussed below, a portion of the spinal rod S is ultimately received within the receiver 14, and a threaded cover T engaging the receiver 14 is positioned over the portion of the spinal rod S to retain the portion of the spinal rod S within the receiver 14. The fastener assembly 10 is similar to that disclosed in U.S. Ser. No. 15/843,938, which is herein incorporated by reference in its entirety.

The screw 12 can be used to facilitate fixed attachment of the receiver 14 and the crown 16 to tissue such as, for example, bone. The screw 12 can be substantially identical to screws disclosed in U.S. Ser. No. 15/843,938. The screws disclosed in U.S. Ser. No. 15/843,938 and the screw 12 can be pedicle screws.

Figure 2:
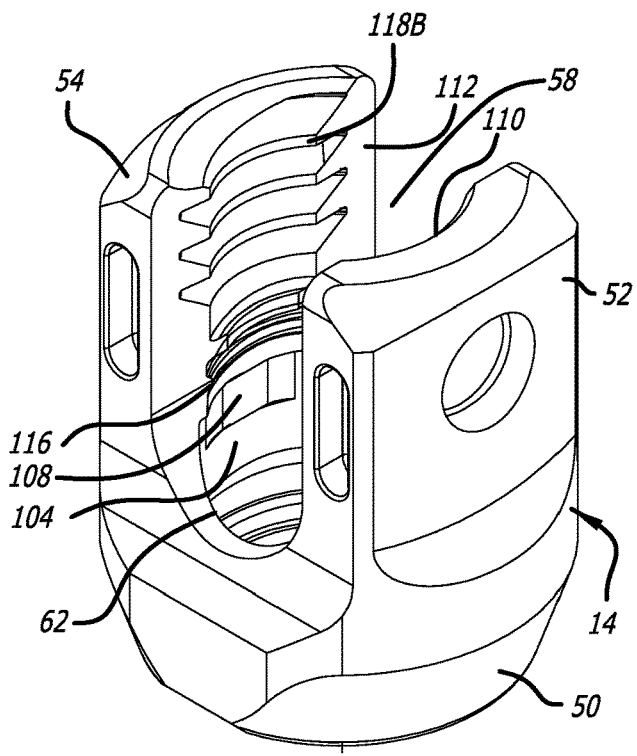
FIG. 2 is a top, front, exploded perspective view that illustrates the pedicle screw assembly of FIG. 1.
Figure 2:
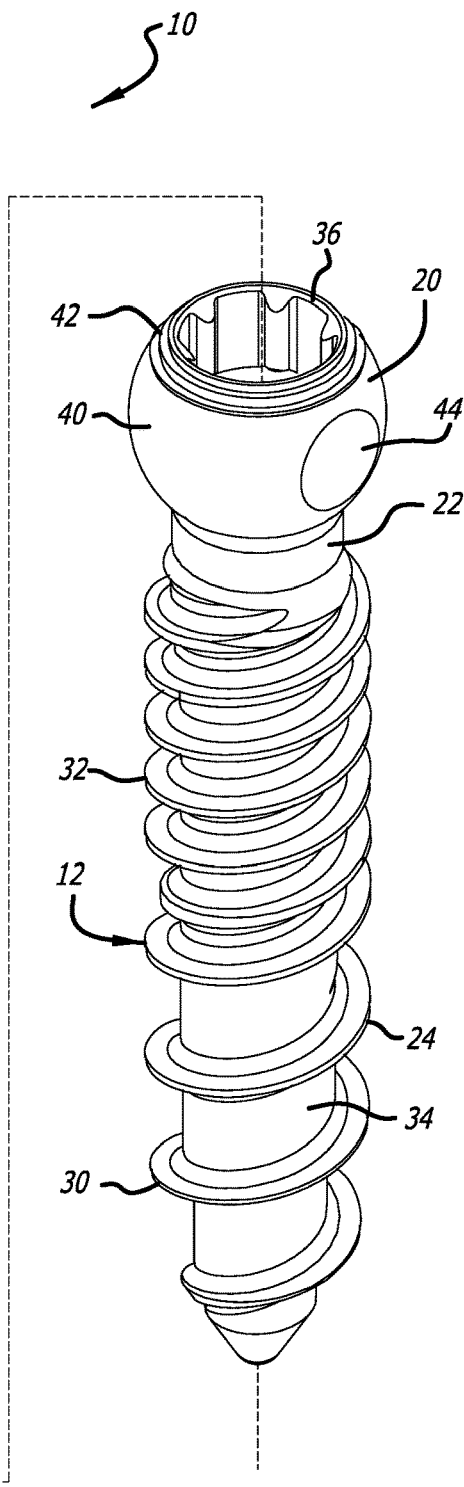
Figure 3:
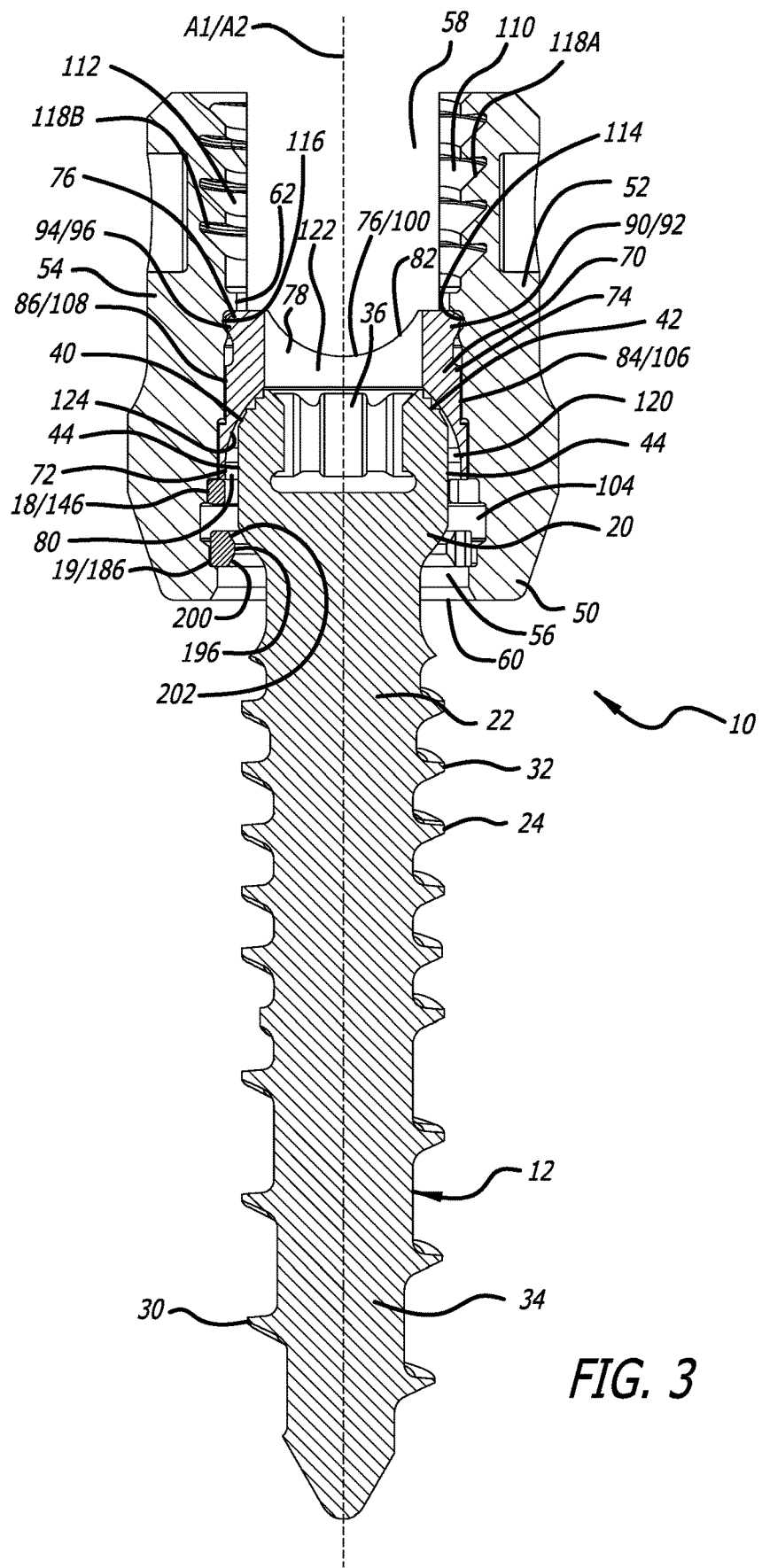
FIG. 3 is a front, elevational, first cross-sectional view that illustrates the pedicle screw assembly of FIG. 1.

The screw 12 includes a head portion 20, a neck portion 22, a shaft portion 24, and a central axis A1. As depicted in FIGS. 1-3, the head portion 20 is generally spherical, the neck portion 22 joins the shaft portion 24 to the head portion 20, and the shaft portion 24 is configured to penetrate tissue such as, for example, bone. The shaft portion 24 can include one or more thread forms having a continuous turn or discrete turns and/or different pitches to facilitate such bone penetration. As depicted in FIGS. 2 and 3, the shaft portion 24 includes a first thread form 30 and a second thread form 32 having a continuous turn and different pitches around a shank 34. Besides facilitating bone penetration, the first thread form 30 and the second thread form 32 are used in securing the screw 12, the receiver 14 and the crown 16 to the bone. Furthermore, the shank 34 can have a smaller or a larger diameter than the neck portion 22, and can include portion(s) having tapered and/or cylindrical configurations.

The head portion 20 includes a tool-engaging portion 36 configured to engage a surgical tool or instrument for rotating the screw 12. The tool-engaging portion 36 includes six (6) lobes arranged in a generally hexagonal cross-sectional configuration. In some embodiments, the tool-engaging portion 36 can have, for example, alternative cross-sectional configurations such as being generally polygonal (including generally triangular, rectangular, hexagonal, etc. configurations), oval, or irregular.

The head portion 20 includes an exterior surface 40, and, as depicted in FIGS. 2 and 3, the exterior surface 40 is generally spherical. The exterior surface 40 includes a plurality of ridges 42 provided adjacent the tool-engaging portion 36 and a plurality of flattened portions 44. The ridges 42 can be used to improve purchase of the head portion 20 with other surgical instrumentation. Furthermore, in some embodiments, the flattened portions 44 can be used to engage protrusions (not shown) in the crown 16 to constrain movement of the screw 12 relative to the crown 16.

As depicted in FIGS. 1-3, the receiver 14 includes a body portion 50, a first arm 52 extending upwardly from the body portion 50, and a second arm 54 extending upwardly from the body portion 50. The receiver 14 includes a first cavity 56 and a second cavity 58. The first cavity 56 is internal to the body portion 50, and extends between a first opening 60 and a second opening 62. The first opening 60 is provided at the end of the body portion 50 opposite from the first arm 52 and the second arm 54, and the second opening 62 is provided at the transition between where the first arm 52 and the second arm 54 extend upwardly from the body portion 50. Furthermore, the second cavity 58 is formed between the first arm 52 and the second arm 54.

As discussed below, in various embodiments, the crown 16 is received in portions of the first cavity 56 and the second cavity 58 in initial stages of assembly of the fastener assembly 10, and then ultimately received in the first cavity 56 due to use of the threaded cover T to retain the portion of the spinal rod S within the receiver 14 and the corresponding interaction of the portion of the spinal rod S with the crown 16. Also, in various embodiments, at least portions of the head portion 20 and the neck portion 22 are ultimately received in the first cavity 56, and the spinal rod S is ultimately received in the second cavity 58.

As depicted in FIGS. 2 and 3, the crown 16 includes a wall portion 70 having a first end 72 and a second end 74, a flange portion 76 extending outwardly from the second end 74 of the wall portion 70, and an internal cavity 78 extending through the wall portion 70 and the flange portion 76 between a first opening 80 formed at the first end 72 of the wall portion 70, and a second opening 82 formed through the flange portion 76. The wall portion 70 can be substantially cylindrical, and includes a first mating portion 84 and a second mating portion 86.

The flange portion 76 can be "saddle" shaped and comprise a first end portion 90 having a first lip portion 92, a second end portion 94 having a second lip portion 96, and a recess 98 formed between the first end portion 90 and the second end portion 94 and defined by a first side surface 100 and a second side surface 102. The first side surface 100 and the second side surface 102 can each be generally U-shaped to provide the flange portion 76 with its "saddle" shape. The recess 98, like the second cavity 58, is configured to receive the portion of the spinal rod S therein. As discussed below, the first mating portion 84 and the second mating portion 86, as well as the first lip portion 92 and the second lip portion 94, can be configured to engage portions of the wall portion 70 in the internal cavity 78 in initial stages of assembly of the fastener assembly 10 to facilitate attachment of the crown 16 to the receiver 14.

As depicted in FIG. 3, the first cavity 56 formed in the body portion 50 is defined by an interior surface 104. The interior surface 104 can be generally cylindrical and be sized to receive at least a portion of the crown 16 therein. The interior surface 104 includes a third mating portion 106 and a fourth mating portion 108 for engaging the first mating portion 84 and the second mating portion 86, respectively. One of the first mating portion 84 and the third mating portion 106 can be a indentation, and the other of the first mating portion 84 and the third mating portion 106 can be a protrusion; and one of the second matting portion 86 and the fourth mating portion 108 can be an indentation, and the other of the second mating portion 86 and the fourth mating portion 108 can be a protrusion. As depicted in FIG. 3, the first mating portion 84 and the second mating portion 86 are indentations, and the third mating portion 106 and the fourth mating portion 108 are protrusions. The engagement of the first mating portion 84 with the third mating portion 106 and of the second mating portion 86 with the fourth mating portion 108 serves in attaching the crown 16 to the receiver 14 in an initial position, as depicted in FIGS. 1 and 3.

As depicted in FIG. 3, the second cavity 58 of the receiver 14 is formed between the first arm 52 and the second arm 54 by a first interior surface 110 formed on the first arm 52 and a second interior surface 112 formed on the second arm 54. The first interior surface 110 includes a first indentation 114 for receiving the first lip portion 92 of the first end portion 90 of the flange portion 76, and the second interior surface 112 includes a second indentation 116 for receiving the second lip portion 96 of the second end portion 94 of the flange portion 76. The engagement of the first lip portion 92 with the first indentation 114 and the second lip portion 96 with the second indentation 116 in the second cavity 58 further serves in attaching the crown 16 to the receiver 14 in the initial position, as depicted in FIGS. 1 and 3. Furthermore, the second cavity 58 includes first threads 118A and second threads 1186 formed on the first interior surface 110 of the first arm 52 and the second interior surface 112 of the second arm 54, respectively, for engaging a threaded cover T for securing the portion of the spinal rod S received in the second cavity 58 relative to the fastener assembly 10.

With continued reference to FIG. 3, the internal cavity 78 of the crown 16 includes a first portion 120 and a second portion 122. The first portion 120 extends from the first opening 80 to a position intermediate the first opening 80 and the second opening 82, and the second portion 122 extends from the position intermediate the first opening 80 and the second opening 82 to the second opening 82. The first portion 120 is sized to receive therein a portion of the head portion 20 of the screw 12, and the second portion 122 is sized to receive a surgical tool or instrument (not shown) for engaging the tool engaging portion 36 when the screw 12 is received in the first portion 120. The first portion 120 is formed by an interior surface 124. As depicted in FIG. 3, the interior surface 124 can be spherical or generally spherical to facilitate engagement with the generally-spherical shape of the exterior surface 40 of the head portion 20. As discussed below, the friction caused by the engagement of the exterior surface 40 (including the ridges 42) with the interior surface 124 serves in maintaining the position of the head portion 20 relative to the crown 16.

Figure 4:
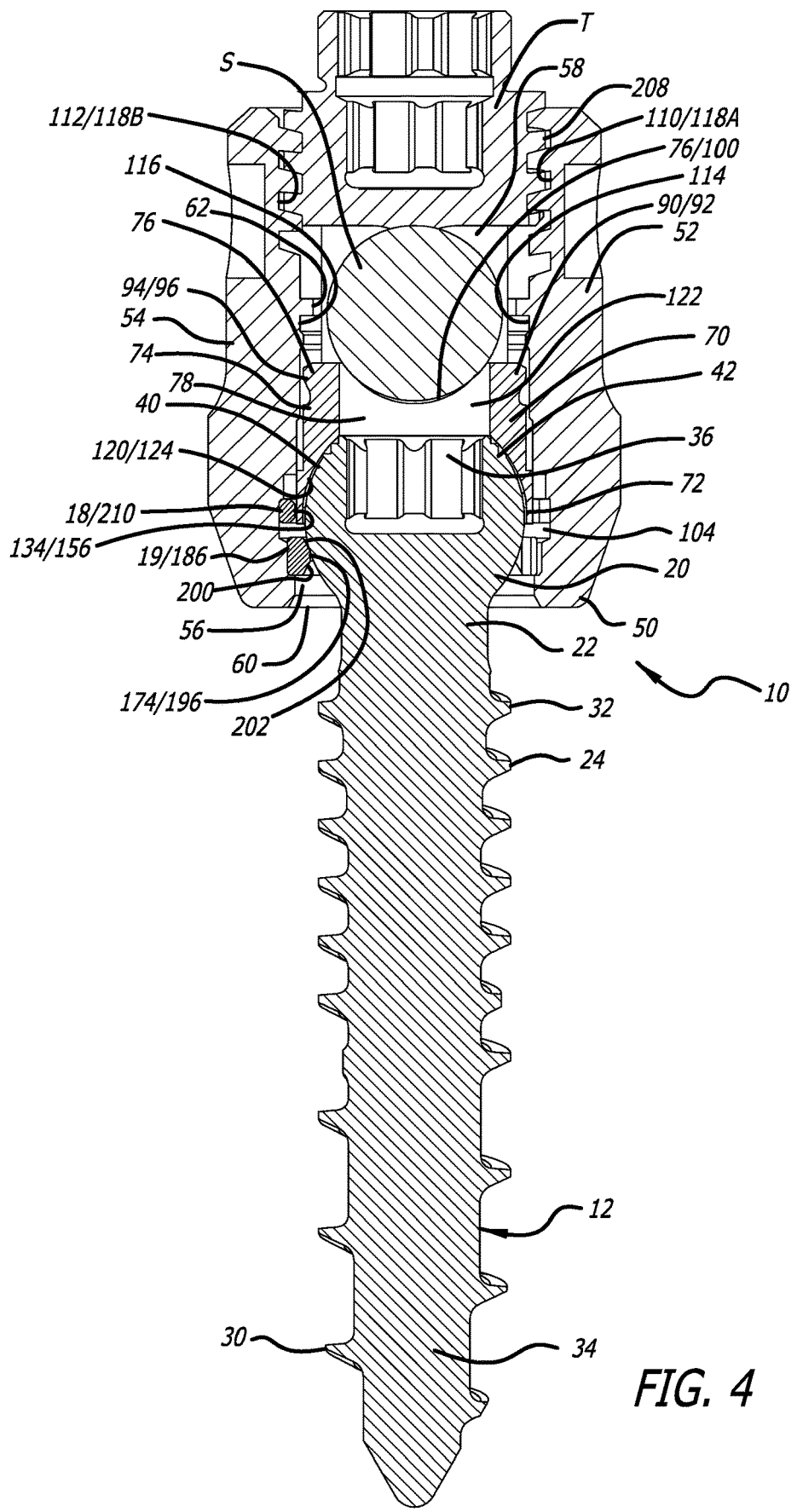
FIG. 4 is a front, elevational, second cross-sectional view that illustrates the pedicle screw assembly of FIG. 1.

The fastener assembly 10, as depicted in FIG. 2, is assembled with the crown 16 first inserted through the first opening 60 and into the first cavity 56, then the first expansion ring 18 is inserted through the first opening 60 and into the first cavity 56, and then the second expansion ring 19 is inserted through the first opening 60 and into the first cavity 56. As discussed below, the crown 16 and the first expansion ring 18 are, first, positioned in the receiver 14 in initial positions as depicted in FIG. 3, and then, after a portion of the head portion 20 of the screw 12 is inserted into the receiver 14, the crown 16 and the first expansion ring 18 are, second, positioned in the receiver 14 in final positions as depicted in FIG. 4 when the threaded cover T pushes the portion of the surgical rod S against the crown 16 and correspondingly pushes the crown 16 against the head portion 20.

The second expansion ring 19, along with the crown 16, are used in ultimately maintaining the position of at least a portion of the screw head portion 20 in the first cavity 56. As discussed below, the first expansion ring 18 and the second expansion ring 19 are in various embodiments each formed as incomplete generally annular structures that afford expansion and contraction thereof. Furthermore, as depicted in FIG. 4, the first expansion ring 18 is configured to ultimately, in use of the resulting assembly 10, aid in holding the crown 16 in position relative to the receiver 14, and in FIG. 4, the second expansion ring 19 is configured to ultimately, in use of the resulting assembly 10, aid in holding the screw 12 in position relative to the crown 16.

As depicted in FIG. 2, the first expansion ring 18 includes a first end 130, an opposite second end 132, and aperture 134 extending between the first end 130 and the second end 132. Furthermore, the first expansion ring 18 is in various embodiments incomplete, and includes a first circumferential end 140, a second circumferential end 142, and a gap 144 between the first circumferential end 140 and the second circumferential end 142. The first expansion ring 18, as discussed above, defines the aperture 134 therethrough, and the first expansion ring 18 is received in a first recess 146 formed in the interior surface 104.

The first expansion ring 18 is compressible to decrease the size of the gap 144, and hence, fit through the first cavity 56 and into the first recess 146. The first expansion ring 18, as depicted in FIG. 2, includes a substantially ring-shaped lower surface 150 at the first end 130, a substantially ring-shaped upper surface 152 at the second end 132, a substantially cylindrical exterior surface 154, and a substantially cylindrical interior surface 156. As depicted in FIG. 3, when the first expansion ring 18 is in the initial position, portions of the upper surface 152 and the exterior surface 154 contact portions of the first recess 146, and portions of the interior surface 156 contact the wall portion 70 of the crown 16. Furthermore, in the initial position thereof, the first expansion ring 18 contacts the crown 16, and serves in maintaining engagement of the first mating portion 84 with the third mating portion 106, engagement of the second mating portion 86 with the fourth mating portion 108, engagement of the first lip portion 92 with the first indentation 114, and engagement of the second lip portion 96 with the second indentation 116.

As depicted in FIG. 2, the second expansion ring 19 includes a first end 170, an opposite second end 172, and an aperture 174 extending between the first end 170 and the second end 172. Furthermore, the second expansion ring 19 is incomplete, and includes a first circumferential end portion 180, a second circumferential end portion 182, and a gap 184 between the first circumferential end portion 180 and the second circumferential end portion 182. The second expansion ring 19, as discussed above, defines the aperture 174 therethrough, and the second expansion ring 19 is received in a second recess 186 formed in the interior surface 104.

The second expansion ring 19 is expandable to increase the size of the gap 184, and hence, increase the size of the aperture 174 to afford passage of at least a portion of the head portion 20 therethrough. After the crown 16 and the first expansion ring 18 are positioned within the receiver 14 in their initial positions, and the second expansion ring 19 is positioned in the second recess 186, at least a portion of the screw head portion 20 can be inserted through the first opening 60, into the first cavity 56, and through the aperture 174. The second expansion ring 19 expands to facilitate passage of at least a portion of the head portion 20 through the aperture 174. If necessary, the second expansion ring 19 can be moved by the head portion 20 from the second recess 186 into a third recess 210 formed between the first recess 146 and the second recess 186. Positioning of the second expansion ring 19 in the third recess 210 affords a further increased size of the aperture 174 to afford passage of at least a portion of the head portion 20 therethrough. The second expansion ring 19 ultimately contracts after passage of at least a portion of the head portion 20 therethrough to facilitate trapping at least a portion of the head portion 20 between the crown 16 and the second expansion ring 19. As discussed below, the friction caused by the ultimate engagement of the head portion 20 with the crown 16 and the second expansion ring 19 and serves in maintaining the position of the head portion 20 relative to the crown 16.

The second expansion ring 19, as depicted in FIG. 2, includes a substantially ring-shaped lower surface 190 at the first end 170, a substantially ring-shaped upper surface 192 at the second end 172, a substantially cylindrical exterior surface 194, and a substantially cylindrical interior surface 196. Portions of the lower surface 190 and the exterior surface 194 contact portions of the second recess 186, and portions of the interior surface 196 contact portions of the head portion 20.

To facilitate passage of at least a portion of the head portion 20 through the aperture 174, the interior surface 196 of the second expansion ring 19 can include a lower angled first surface 200 adjacent the first end 170. As depicted in FIG. 2, the lower angled first surface 200 can be an incomplete frusto-conical shape. The configuration of the lower angled first surface 200 serves to aid expansion of the second expansion ring 19 as at least a portion of the head portion 20 pass thereby.

Furthermore, to facilitate maintenance of the position of at least a portion of the head portion between the crown 16 and the second expansion ring 19, the interior surface 196 of the second expansion ring 19 can include an upper angled second surface 202 adjacent the second end 172. As depicted in FIG. 2, the upper angled second surface 202 can be an incomplete frusto-conical shape.

When the crown 16 and the first expansion ring 18 are positioned in the receiver 14 in the final positions depicted in FIG. 4, the configurations of interior surface 124 and the upper angled second surface 202 serve in maintaining the screw 12 in a selected angular position relative to the receiver 14 and the crown 16. That is, the friction of the caused by the interface of the exterior surface 40 (including the ridges 42) on the interior surface 124 and the friction caused by the interface of the exterior surface 40 on the upper angled second surface 202 serves to resist movement of the head portion 20 (and the remainder of the screw 12) relative to the receiver 14 and the crown 16. As such, this friction serves to maintain a selected position of the screw 12 relative to the receiver 14 and the crown 16.

During use of the fastener assembly 10, the screw 12 can be attached to bone prior to attachment of the receiver 14 and the crown 16 thereto, the receiver 14 and the crown 16 can be attached to the screw 12 prior to attachment of the screw to bone, or the screw 12 can be initially attached to bone, the receiver 14 and the crown 16 can then be attached to screw 12, and the screw 12 (with the receiver 14 and the crown 16 attached thereto can further be attached to the bone.

To facilitate positioning of the crown 16 in its initial position (FIG. 3) relative to the receiver 14, the crown 16 is inserted through the first opening 60, into the first cavity 56, so that the first mating portion 84 is engaged with the third mating portion 106, the second mating portion 86 is engaged with the fourth mating portion 108, the first lip portion 92 is engaged with the first indentation 114, the second lip portion 96 is engaged with the second indentation 116. To facilitate positioning of the first expansion ring 18 in its initial position (FIG. 3) relative to the receiver 14, the first expansion ring 18 thereafter is inserted through the first opening 60 and into the first cavity 56, and positioned in the first recess 146 formed in the interior surface 104. After the crown 16 and the first expansion ring 18 are positioned in the initial positions as depicted in FIG. 3, the second expansion ring is inserted through the first opening 60 into the first cavity 56, and positioned in the second recess 186 formed in the interior surface 104.

The facilitate attachment of the screw 12 to the receiver 14 and the crown 16, at least a portion of the head portion 20 is inserted through the first opening 60, into the first cavity 56, and through the aperture 134 (with the second expansion ring 19 expanding as necessary to afford insertion therethrough). If necessary, the second expansion ring 19 is moved by the head portion 20 from the second recess 186 into the third recess 210 to afford a further increased size of the aperture 174.

After at least a portion of the head portion 20 is received in the first cavity 56, and the portion of the surgical rod S is positioned in the second cavity 58 and is contacted with the crown 16 at the first side surface 100 and the second side surface 102 thereof, threads 208 of the threaded cover are threadably engaged to the first threads 118A and second threads 118B. As depicted in FIG. 4, when the threaded cover pushes the portion of the surgical rod S against the crown 16, the first mating portion 84, the second mating portion 86, the first lip portion 92, and the second lip portion 96 are released from their above-discussed engagement with receiver 14, and the crown 16 is moved downwardly within the receiver 14. Such movement of the crown 16 forces the first expansion ring 18 from the first recess 146 into the third recess 210, and pushes the interior surface 124 against the exterior surface 40 (including the ridges 42) and the exterior surface 40 against the upper angled surface 202 to trap at least a portion of the head portion 20 between the crown 16 and the second expansion ring 19. If the expansion ring 19 is located in the third recess 210, such movement forcing the exterior surface 40 against the upper angled surface 202 pushes the second expansion ring 19 from the third recess 210 into the second recess 186 to contract the second expansion ring 19. The first expansion ring 18 is configured to ultimately aid in holding the crown 16 in position relative to the receiver 14 via friction. Furthermore, friction between the screw 12 and the second expansion ring 19, and friction between the screw 12 and the crown 16 can serve in maintaining the position of the screw 14 relative to the remainder of the fastener assembly 10.

Increasing surface roughness of components of the fastener assembly 10 can increase performance characteristics thereof, and to illustrate, the following component interfaces of the fastener assembly 10 can benefit from such increased surface roughness. For example, increased friction between the second expansion ring 19 and the screw 12 at the interface of the exterior surface 40 of the head portion 20 on the upper angled second surface 202, increased friction between the screw 12 and the crown 16 at the interface of the exterior surface 40 (including the ridges 42) on the interior surface 124, increased friction between the first expansion ring 18 and the receiver 14 at the interface of the first expansion ring 18 with the first recess 146, increased friction between the second expansion ring 19 and the receiver 14 at the interface of the second expansion ring 19 with the second recess 186, and increased friction between the crown 16 and the spinal rod S at the interface of the spinal rod S with the first side surface 100 and the second side surface 102 can be beneficial to the fastener assembly 10. To that end, the crown 16, the first expansion ring 18, and/or the second expansion ring 19 can be manufactured via a 3D printing, or additive-manufacturing, process. Printing the respective parts can be referred to as separate processes—e.g., in the claims, hereof—whether the printings share steps or functions, and are performed at the same or proximate time/s and location/s.

To illustrate, 3D printing processes can create roughened surfaces during the formation of the receiver 14, the crown 16, the first expansion ring 18, and/or the second expansion ring 19 superior to those capable of being created via other manufacturing processes such as media blasting processes or machining processes. 3D printing can be used in optimizing the surface characterization of components of the fastener assembly 10 by increasing the Ra to a range between about 0.8 μm (32 μin) to about 3.2 μm (125 μin), where Ra is the arithmetic average of the roughness profile. By providing the above-discussed Ra range via 3D printing, the coefficients of frictions between the components of the fastener assembly 10 can correspondingly be increased.

These roughened surfaces manufactured using 3D printing when interfaced with other similarly formed roughened surfaces, roughened surfaces created via other manufacturing process, and smoothened surfaces provide advantageous Ra's and coefficient of friction increases that afford mechanical advantages that mitigate trade-offs in the configuration of the fastener assembly 10.

To illustrate, decapitation strengthen the receiver 14 relative to the screw 12, and maximum angulation of the receiver 14 relative to the screw 12 are competing trade-offs. Decapitation strength is the force required to pull the receiver 14 from the screw 12, and the maximum angulation of the receiver 14 relative to the screw 12 is the maximum angle of the axis $A_2$ of the receiver 14 with respect to the axis $A_1$ of the screw 12. Typically, as the maximum angulation of the receiver 14 relative to the screw 12 is increased, the decapitation strength of the receiver 14 relative to the screw 12 is decreased. The use of 3D printing to manufacture, for example, the second expansion ring 19 to create roughened surfaces thereon can increase the coefficient of friction between the upper angled surface 202 and the head portion 20, and such friction can provide better mechanical performance to mitigate this trade-off and increase both the decapitation strength and the maximum angulation. For example, the Ra of the upper angled surface 202 can be in the range between about 0.8 μm (32 μin) to about 3.2 μm (125 μin), and such a range can afford increasing of the inner diameter (ID) of the second expansion 19 to increase so that the maximum angle of the axis $A_2$ of the receiver 14 with respect to the axis $A_1$ of the screw 12 can be increased from approximately 25° to approximately 35°.

Manufacturing using 3D printing can also increase other performance characteristics of the pedicle screw assemblies. To illustrate, manufacturing the receiver 14, the crown 16, the first expansion ring 18, and/or the second expansion ring 19 using 3D printing to have Ra's in the above-discussed range can increase the coefficient of friction of the receiver 14 and the crown 16 at the interface therebetween, increase the coefficient of friction between the screw 12 and the crown 16 at the interface of the exterior surface 40 (including the ridges 42) on the interior surface 124, increase the coefficient of friction between the first expansion ring 18 and the receiver 14 at the interface of the first expansion ring 18 with the first recess 146, increase the coefficient of friction (to increase ball-slip strength) between the second expansion ring 19 and the receiver 14 at the interface of the second expansion ring 19 with the second recess 186, and increase the coefficient of friction (to increase axial grip and torsional strength) between the crown 16 and the spinal rod S received in the recess 98 at the first side surface 100 and the second side surface 102.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A bone fastener assembly comprising:
a bone screw including a head portion, a threaded shaft portion, and a central axis, the head portion including an exterior surface;
a receiver including a body portion having a first end, an opposite second end, and an interior surface defining a first cavity extending between the first end and the second end;
a crown including a first end, an opposite second end, an exterior surface, and an interior surface defining at least a first interior cavity portion extending from the first end of the crown to a position intermediate the first end and the second end of the crown; and
a retaining ring having an annular shape and including a generally cylindrical exterior surface, an upwardly-facing interior surface, a downwardly-facing interior surface, and a generally cylindrical interior surface between the upwardly-facing interior surface and the downwardly-facing interior surface; and
an expansion ring having an annular shape and including a generally cylindrical exterior surface and a generally cylindrical interior surface;
wherein, when the bone fastener assembly is assembled,
at least a portion of the crown is positioned within the first cavity of the receiver at a position at and adjacent the second end of the body portion,
the retaining ring is positioned within the first cavity of the receiver at a position between the crown and the first end of the body portion,
the expansion ring is positioned within the first cavity of the receiver at a position between the second end of the body portion and the retaining ring,
at least a portion of the head portion is receivable between the crown and the retaining ring,
the exterior surface the head portion contacts the upwardly-facing surface of the retaining ring,
wherein the retaining ring has a maximum outside diameter at the generally cylindrical exterior surface thereof and a minimum inside diameter at the generally cylindrical interior surface thereof, and the expansion ring has a maximum outside diameter at the generally cylindrical interior surface thereof and a minimum inside diameter at the generally cylindrical interior surface thereof, the maximum outside diameter of the retaining ring being smaller than the maximum outside diameter of the expansion ring, and the minimum inside diameter of the retaining ring being smaller than the minimum inside diameter of the expansion ring, and wherein the retaining ring is manufactured using a first 3D printing process that provides for a Ra (Surface Finish) of at least the upwardly-facing surface of the retaining ring ranging from about 0.8 µm (32 µin) to about 3.2 µm (125 µin).

2. The bone fastener assembly of claim 1, wherein the exterior surface of the head portion is substantially spherical and the upwardly-facing surface of the retaining ring is substantially frusto-conical.

3. The bone fastener assembly of claim 1, wherein, when the bone fastener assembly is assembled, the exterior surface of the head portion contacts the interior surface of the crown, and wherein the crown is manufactured using a second 3D printing process that provides for a Ra (surface finish) of at least the interior surface of the crown ranging from about 0.8 µm (32 µin) to about 3.2 µm (125 µin).

4. The bone fastener assembly of claim 3, wherein the receiver is manufactured using a third 3D printing process that provides for a Ra (surface finish) of at least the interior surface of the receiver ranging from about 0.8 µm (32 µin) to about 3.2 µm (125 µin).

5. The bone fastener assembly of claim 1, wherein the interior surface of the receiver includes a first recess for receiving the retaining ring therein, and the receiver is manufactured using a second 3D printing process that provides for a Ra (surface finish) of at least the interior surface of the receiver ranging from about 0.8 µm (32 µin) to about 3.2 µm (125 µin).

6. The bone fastener assembly of claim 1, wherein the expansion ring is manufactured using a second 3D printing process that provides for a Ra (surface finish) ranging from about 0.8 µm (32 µin) to about 3.2 µm (125 µin), and the interior surface of the receiver includes a second recess for receiving the expansion ring therein.

7. The bone fastener assembly of claim 6, wherein, when the bone fastener assembly is assembled, at least a portion of the crown contacted with the expansion ring, and wherein the crown is manufactured using a third 3D printing process that provides for a Ra (surface finish) ranging from about 0.8 µm (32 µin) to about 3.2 µm (125 µin).

8. A bone fastener assembly comprising:
a bone screw including a head portion, a threaded shaft portion, and a central axis, the head portion including an exterior surface;
a receiver including a body portion, a first arm portion, and a second arm portion, the body portion having a first end, an opposite second end, and an interior surface defining a first cavity extending between the first end and the second end, the first arm portion including a first interior arm surface and the second arm portion including a second interior arm surface, the first interior arm surface and the second interior arm surface defining a second cavity therebetween, the first cavity and the second cavity communicating with one another;
a crown including a first end, an opposite second end, an exterior surface, and an interior surface defining at least a first interior cavity portion extending from the first end of the crown to a position intermediate the first end and the second end of the crown;
a retaining ring having an annular shape and including a generally cylindrical exterior surface, an upwardly-facing interior surface, a downwardly-facing interior surface, and a generally cylindrical interior surface between the upwardly-facing interior surface and the downwardly-facing interior surface; and
an expansion ring having an annular shape and including a generally cylindrical exterior surface and a generally cylindrical interior surface;
wherein, when the bone fastener assembly is assembled, the retaining ring is positioned within the first cavity of the receiver at a position between the crown and the first end of the body portion,
the expansion ring is positioned within the first cavity of the receiver at a position between the second end of the body portion and the retaining ring;
at least a portion of the crown is received within the expansion ring;
at least a portion of the head portion is receivable between the crown and the retaining ring, and
the exterior surface the head portion contacts the upwardly-facing surface of the retaining ring;
wherein the retaining ring has a maximum outside diameter at the generally cylindrical exterior surface thereof and a minimum inside diameter at the generally cylindrical interior surface thereof, and the expansion ring has a maximum outside diameter at the generally cylindrical interior surface thereof and a minimum inside diameter at the generally cylindrical interior surface thereof, the maximum outside diameter of the retaining ring being smaller than the maximum outside diameter of the expansion ring, and the minimum inside diameter of the retaining ring being smaller than the minimum inside diameter of the expansion ring, and wherein the retaining ring is manufactured using a first 3D printing process that provides for a Ra (surface finish) of at least the upwardly-facing surface of the retaining ring ranging from about 0.8 µm (32 µin) to about 3.2 µm (125 µin), and wherein the expansion ring is manufactured using a second 3D printing process that provides for Ra (surface finish) ranging from about 0.8 µm (32 µin) to about 3.2 µm (125 µin).

9. The bone fastener assembly of claim 8, wherein the exterior surface of the head portion is substantially spherical and the upwardly-facing surface of the retaining ring is substantially frusto-conical.

10. The bone fastener assembly of claim 8, wherein, when the bone fastener assembly is assembled, the exterior surface of the head portion contacts the interior surface of the crown, and wherein the crown is manufactured using a third 3D printing process that provides for a Ra (surface finish) of at least the interior surface of the crown ranging from about 0.8 µm (32 µin) to about 3.2 µm (125 µin).

11. The bone fastener assembly of claim 10, wherein the receiver is manufactured using a fourth 3D printing process that provides for a Ra (surface finish) of at least the interior surface of the receiver ranging from about 0.8 µm (32 µin) to about 3.2 µm (125 µin).

12. The bone fastener assembly of claim 8, wherein the interior surface of the receiver includes a first recess for receiving the retaining ring therein, and the receiver is manufactured using a 3D printing process that provides for a Ra (surface finish) of at least the ranging from about 0.8 µm (32 µin) to about 3.2 µm (125 µin).

13. The bone fastener assembly of claim 12, wherein the interior surface of the receiver includes a second recess for receiving the expansion ring therein, and the expansion ring is manufactured using a fourth 3D printing process that provides for a the Ra (surface finish) ranging from about 0.8 µm (32 µin) to about 3.2 µm.

14. The bone fastener assembly of claim 13, wherein the crown is manufactured using a fifth 3D printing process that provides for a Ra (surface finish) ranging from about 0.8 µm (32 µin) to about 3.2 µm (125 µin).

15. A bone fastener assembly comprising:
- a bone screw including a head portion, a threaded shaft portion, and a central axis, the head portion including an exterior surface;
- a receiver including a body portion having a first end, an opposite second end, and an interior surface defining a first cavity extending between the first end and the second end; and
- a retaining ring having an annular shape and including a generally cylindrical exterior surface, a generally cylindrical interior surface, and an upwardly-facing surface;
- an expansion ring having an annular shape and including a generally cylindrical exterior surface and a generally cylindrical interior surface;
- wherein, when the bone fastener assembly is assembled,
- the retaining ring is positioned within the first cavity of the receiver at a position between the first end and the second end of the body portion,
- the expansion ring is positioned within the first cavity of the receiver at a position between the second end of the body portion and the retaining ring,
- at least a portion of the head portion is receivable between the retaining ring and the second end of the body portion, and
- the exterior surface the head portion contacts the upwardly-facing surface of the retaining ring;
- wherein the retaining ring has a maximum outside diameter at the generally cylindrical exterior surface thereof and a minimum inside diameter at the generally cylindrical interior surface thereof, and the expansion ring has a maximum outside diameter at the generally cylindrical interior surface thereof and a minimum inside diameter at the generally cylindrical interior surface thereof, the maximum outside diameter of the retaining ring being smaller than the maximum outside diameter of the expansion ring, and the minimum inside diameter of the retaining ring being smaller than the minimum inside diameter of the expansion ring, and
- wherein the retaining ring is manufactured using a first 3D printing process that provides for a Ra (surface finish) of at least the upwardly-facing surface of the retaining ring ranging from about 0.8 µm (32 µin) to about 3.2 µm (125 µin).

16. The bone fastener assembly of claim 15, wherein the exterior surface of the head portion is substantially spherical and the upwardly-facing surface of the retaining ring is substantially frusto-conical.

17. The bone fastener assembly of claim 16, further comprising a crown including a first end, an opposite second end, an exterior surface, and an interior surface defining at least a first interior cavity portion extending from the first end of the crown to a position intermediate the first end and the second end of the crown, wherein at least a portion of the crown is positioned within the first cavity of the receiver at a position at and adjacent the second end of the body portion, and the at least a portion of the head portion is receivable between the crown and the retaining ring.

18. The bone fastener assembly of claim 17, wherein, when the bone fastener assembly is assembled, the exterior surface of the head portion contacts the interior surface of the crown, and wherein the crown is manufactured using a second 3D printing process that provides for a Ra (surface finish) of at least the interior surface of the crown ranging from about 0.8 µm (32 µin) to about 3.2 µm (125 µin).

19. The bone fastener assembly of claim 18, wherein the receiver is manufactured using a third 3D printing process that provides for a Ra (surface finish) of at least the interior surface of the receiver ranging from about 0.8 µm (32 µin) to about 3.2 µm (125 µin).

20. The bone fastener assembly of claim 15, wherein the interior surface of the receiver includes a first recess for receiving the retaining ring therein, and the receiver is manufactured using a second 3D printing process that provides for a Ra (surface finish) of at least the interior surface of the receiver ranging from about 0.8 µm (32 µin) to about 3.2 µm (125 µin).

* * * * *